United States Patent
Williams et al.

[11] Patent Number: 5,931,774
[45] Date of Patent: Aug. 3, 1999

[54] INFLATABLE DEVICES FOR TUMOR TREATMENT

[75] Inventors: Jeffery A. Williams, Baltimore, Md.; Christopher H. Porter, Woodinville, Wash.; Mark A. Rydell, Golden Valley, Minn.

[73] Assignee: Proxima Therapeutics, Inc., Alpharetta, Ga.

[21] Appl. No.: 08/727,259

[22] Filed: Oct. 7, 1996

Related U.S. Application Data

[63] Continuation-in-part of application No. 08/307,165, Sep. 14, 1994, Pat. No. 5,611,767, which is a continuation of application No. 07/715,923, Jun. 14, 1991, Pat. No. 5,429,582.

[51] Int. Cl.⁶ ..................................................... A61N 5/02
[52] U.S. Cl. ............................................................ 600/2
[58] Field of Search ........................ 600/1–8; 604/19–20; 607/1–3, 88, 96, 99, 100, 103, 105, 107, 113, 114

[56] References Cited

U.S. PATENT DOCUMENTS

| | | | |
|---|---|---|---|
| 2,043,630 | 6/1936 | Raiche | 18/58 |
| 2,677,375 | 5/1954 | Raiche | 128/349 |
| 3,173,418 | 3/1965 | Baran | 128/351 |
| 3,324,847 | 6/1967 | Zoumboulis | 128/1.2 |
| 3,640,269 | 2/1972 | Delgado | 128/2 |
| 3,831,629 | 8/1974 | Mackal et al. | 137/525 |
| 3,872,856 | 3/1975 | Clayton | 128/1.2 |
| 4,022,190 | 5/1977 | Meyer | 128/2 A |
| 4,085,757 | 4/1978 | Pevsner | 604/96 |
| 4,103,689 | 8/1978 | Leighton | 128/350 V |
| 4,133,315 | 1/1979 | Berman et al. | 604/96 |
| 4,206,762 | 6/1980 | Cosman | 128/660 |
| 4,213,461 | 7/1980 | Pevsner | 128/348 |
| 4,217,889 | 8/1980 | Radovan et al. | 128/1 |
| 4,281,667 | 8/1981 | Cosman | 128/348 |
| 4,292,960 | 10/1981 | Paglione | 128/1.1 |
| 4,382,445 | 5/1983 | Sommers | 604/8 |
| 4,417,576 | 11/1983 | Baran | 128/207.15 |
| 4,541,429 | 9/1985 | Prosl et al. | 604/249 |

(List continued on next page.)

FOREIGN PATENT DOCUMENTS

| | | |
|---|---|---|
| 0 205 384 | 12/1986 | European Pat. Off. . |
| 0 340 881 | 11/1989 | European Pat. Off. . |
| 0 366 814 | 5/1990 | European Pat. Off. . |
| 37 25 691 | 3/1988 | Germany . |
| 2 105 201 | 3/1983 | United Kingdom . |

(List continued on next page.)

OTHER PUBLICATIONS

Exhibit A—catalog page of American Heyer–Schulte.
Garfield, et al., "Postoperative intracavitary chemotherapy of malignant glimos", *J. Neurosurg.*, vol. 39, Sep., 1973, pp. 315–322.
*NASA Tech Briefs*, Jun., 1990, at p. 106.
Shimm et al., "Scanned Focessed Ultrasound Hyperthermia: Initial Crucial Results", *Int. J. Radiation Oncology Bio. Phys.*, Nov. 1988, vol. 15, pp. 1203–1208.
Roberts et al., "Interstitial hyperthermia and iridium brachytherapy in treatment of malignant gliomas" *J. Neorosurg.*, vol. 64, Apr. 1986.

(List continued on next page.)

*Primary Examiner*—John P. Lacyk
*Attorney, Agent, or Firm*—Thomas J. Engellenner; Nutter, McClennen & Fish,LLP

[57] ABSTRACT

Implantable devices for treatment of proliferative disorders are described. In one aspect, the invention provides an implantable apparatus for treating a proliferative disorder in a patient. The device comprises a treatment fluid receptacle for receiving a treatment fluid, an inflatable balloon having a balloon body, a catheter connected between the treatment fluid receptacle and the balloon and defining a fluid flow path therebetween, and a diffusion barrier disposed in the fluid flow path between the treatment fluid receptacle and the balloon. Methods for treating proliferative disorders with the devices are also disclosed.

43 Claims, 2 Drawing Sheets

U.S. PATENT DOCUMENTS

| | | | |
|---|---|---|---|
| 4,558,693 | 12/1985 | Lash et al. | 128/79 |
| 4,564,022 | 1/1986 | Rosenfeld et al. | 128/748 |
| 4,588,394 | 5/1986 | Schulte et al. | 604/9 |
| 4,593,703 | 6/1986 | Cosman | 128/748 |
| 4,601,713 | 7/1986 | Fuqua | 604/280 |
| 4,602,655 | 7/1986 | Mackal | 137/515 |
| 4,617,015 | 10/1986 | Foltz | 604/100 |
| 4,619,247 | 10/1986 | Inoue et al. | 128/6 |
| 4,653,508 | 3/1987 | Cosman | 128/748 |
| 4,655,745 | 4/1987 | Corbett | 604/49 |
| 4,655,748 | 4/1987 | Mushika | 604/96 |
| 4,660,568 | 4/1987 | Cosman | 128/748 |
| 4,681,132 | 7/1987 | Lardner | 137/271 |
| 4,681,560 | 7/1987 | Schulte et al. | 604/9 |
| 4,699,615 | 10/1987 | Fischell et al. | 604/131 |
| 4,706,652 | 11/1987 | Horowitz | 128/1.2 |
| 4,710,177 | 12/1987 | Smith et al. | 604/185 |
| 4,754,745 | 7/1988 | Horowitz | 128/1.2 |
| 4,754,752 | 7/1988 | Ginsburg et al. | 128/303.12 |
| 4,763,642 | 8/1988 | Horowitz | 128/1.2 |
| 4,776,369 | 10/1988 | Lardner et al. | 137/515.5 |
| 4,788,063 | 11/1988 | Fisher et al. | 424/449 |
| 4,800,899 | 1/1989 | Elliott | 600/2 |
| 4,816,016 | 3/1989 | Schulte et al. | 604/9 |
| 4,821,725 | 4/1989 | Azam et al. | 128/420 |
| 4,846,191 | 7/1989 | Brockway et al. | 128/748 |
| 4,867,741 | 9/1989 | Portnoy | 604/10 |
| 5,084,015 | 1/1992 | Moriuchi | 604/96 |
| 5,106,360 | 4/1992 | Ishiwara et al. | 600/2 |
| 5,112,303 | 5/1992 | Pudenz et al. | 604/49 |
| 5,125,888 | 6/1992 | Howard et al. | 600/12 |
| 5,152,747 | 10/1992 | Olivier | 604/93 |
| 5,236,410 | 8/1993 | Granov et al. | 600/12 |
| 5,429,582 | 7/1995 | Williams | 600/2 |

FOREIGN PATENT DOCUMENTS

| | | |
|---|---|---|
| WO 90 04365 | 5/1990 | WIPO. |
| WO 91 05528 | 5/1991 | WIPO. |
| WO 92 10932 | 7/1992 | WIPO. |
| 92/22350 | 12/1992 | WIPO. |
| WO 93 09724 | 5/1993 | WIPO. |

OTHER PUBLICATIONS

Chun et al., "Interstitial iridum–192 implantation for malignant brain tumours Part II", *The British Journal of Radiology*, Feb., 1989, pp. 158–162.

*Am. J. Clin. Oncol., (CCT)*, vol. 10, No. 2, 1987, at p. 106, item (13).

Gutin et al. "Brachytherapy of recurrent malignant brain tumors with removable high–activity iodine–125 sources", *J. Neurosurg*, vol. 60, pp. 61–68, Jan. 1984.

Wu et al., "Interstitial iridium–192 implantation for malignant brain tumours Part I", *The British Journal of Radiology*, pp. 154–157, Feb. 1989.

Raaphorst et al. "A Comparison of Heat and Radiation Sensitivity of Three Human Glioma Cell Lines", *J. Radiation Oncology Biol. Phys.*, vol. 17, pp. 615–622.

Moidel et al., "Materials for Selective Tissue Heating in a Radiofrequency Electromagnetic Field for the Combined Chemothermal Treatment of Brain Tumors", *J. Biomed Mater. Res.*, vol. 10, pp. 327–334, 1976.

Exhibit B—Brochure of Halkey–Roberts Corporation of St. Petersburg, Florida.

European Search Report Application No. EP 92 91 3085 dated Dec. 12, 1995.

INFLATABLE DEVICES FOR TUMOR TREATMENT

RELATED APPLICATIONS

This application is a continuation-in-part of U.S. Ser. No. 08/307,165, filed Sep. 14, 1994, now U.S. Pat. No. 5,611,767, which is a continuation of U.S. Ser. No. 07/715,923, filed Jun. 14, 1991, now U.S. Pat. No. 5,429,582, the contents of which are hereby incorporated by reference.

BACKGROUND OF THE INVENTION

Treatment of proliferative disorders has become increasingly sophisticated in recent years, and improvements in surgical, chemotherapeutic and brachytherapeutic techniques have led to better outcomes in patients suffering from such disorders. The need for improved devices for administration of chemotherapy and brachytherapy has resulted in a number of new devices capable of delivering one or more treatments to proliferative disease sites, such as tumors. One such device is described in U.S. Pat. No. 5,429,582 to Williams, which discloses an inflatable device for multimodal therapy of tumors. Nevertheless, improved devices for treatment of proliferative disorders are needed.

SUMMARY

This invention provides improved devices for the treatment of tumors and other proliferative disorders in a patient in need of such treatment, and methods of treating proliferative disorders using such devices.

In one aspect, the invention provides an implantable apparatus for treating a proliferative disorder in a patient. The device comprises a treatment fluid receptacle for receiving a treatment fluid, an inflatable balloon having a balloon body, a catheter connected between the treatment fluid receptacle and the balloon and defining a fluid flow path therebetween, and a diffusion barrier disposed in the fluid flow path between the treatment fluid receptacle and the balloon.

In certain embodiments, the treatment fluid receptacle has a small volume and is adapted to be implanted subcutaneously in the body of the patient. In certain embodiments, the device further includes a malleable element. In certain embodiments, the diffusion barrier is a narrow flow segment. In certain embodiments, the balloon has a substantially spherical shape when inflated. In other embodiments, the balloon has a substantially ovoid shape when inflated. In some embodiments, the balloon is secured to the catheter at substantially a single point on the balloon body. In other embodiments, the balloon is secured to the catheter at a plurality of points on the balloon body. In certain embodiments, the balloon has an irregular shape when inflated.

The balloon body can be substantially impermeable to the treatment fluid, while in other embodiments, the balloon can comprise a semipermeable membrane. In certain embodiments, the treatment fluid receptacle can be flushed with a flushing fluid without substantially expanding the balloon. In some embodiments, the balloon is secured to the catheter such that the balloon maintains a pre-selected shape during inflation. In preferred embodiments, the malleable element, if present, does not interfere with NMR measurements.

In certain embodiments, the balloon comprises a double-walled balloon or a triple-walled balloon. In some embodiments, the proliferative disorder is a brain tumor. In certain embodiments, the balloon is adapted for placement in a cavity left by surgical removal of a tumor from the patient. In other embodiments, the balloon is adapted for placement in a natural body cavity. In preferred embodiments, the balloon is filled with a treatment fluid. In certain embodiments, the treatment fluid is a radioactive fluid. In some embodiments, the treatment fluid has substantially physiological tonicity.

In certain embodiments, the apparatus further comprises a second treatment fluid receptacle. In certain embodiments, the second treatment fluid receptacle fluidly communicates with a volume between inner and outer balloon walls.

In another embodiment, the invention provides an implantable apparatus for treating a proliferative disorder in a patient. The implantable apparatus includes a treatment fluid receptacle for receiving a treatment fluid, an inflatable balloon having a balloon body; a catheter connected between the treatment fluid receptacle and the balloon and defining a fluid flow path therebetween; and a diffusion barrier disposed in the fluid flow path between the treatment fluid receptacle and the balloon, and in which the balloon is secured to the catheter such that the balloon maintains a pre-selected shape during inflation; and in which the treatment fluid receptacle is adapted to be flushed with a small volume of a flush fluid.

In another aspect, the invention provides a method for treating a proliferative disorder, such as a tumor, in a patient. The method includes the steps of implanting in the patient's body an inflatable treatment apparatus, in which the apparatus includes a treatment fluid receptacle for receiving a treatment fluid; an inflatable balloon having a balloon body; a catheter connected between the treatment fluid receptacle and the balloon and defining a fluid flow path therebetween; and a diffusion barrier disposed in the fluid flow path between the treatment fluid receptacle and the balloon; and introducing a treatment fluid into the treatment fluid receptacle such that the balloon is inflated; such that the proliferative disorder is treated.

In certain embodiments, the method includes the further step of flushing the treatment fluid into the balloon.

In another aspect, the invention provides a method for treating a proliferative disorder in a patient. The method comprises determining a characteristic of a cavity in the patient's body, the characteristic being selected from the group consisting of volume, shape, or a dimension; selecting an inflatable balloon suitable for placement in the cavity, the balloon including a balloon body. The method includes the further steps of implanting in the cavity an inflatable treatment apparatus comprising a treatment fluid receptacle for receiving a treatment fluid; the inflatable balloon; a catheter connected between the treatment fluid receptacle and the balloon and defining a fluid flow path therebetween; and a diffusion barrier disposed in the fluid flow path between the treatment fluid receptacle and the balloon. The method further includes the step of introducing a treatment fluid into the treatment fluid receptacle such that the balloon is inflated, such that the proliferative disorder is treated.

In certain embodiments, the method includes, prior to the implanting step, the further step of assembling the inflatable treatment apparatus.

DETAILED DESCRIPTION OF THE INVENTION

Figure 1:
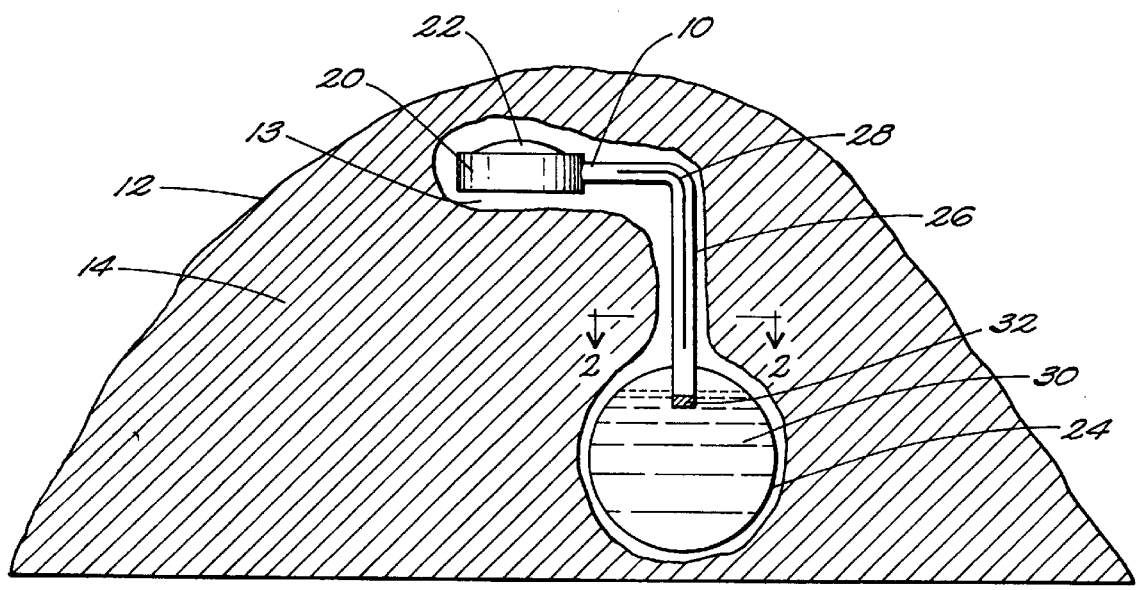
FIG. 1 is a schematic cross-sectional view of one embodiment of the treatment devices of the invention.

The ability to selectively deliver therapy to a target organ or site, e.g., a tumor, is of great value to physicians. Accordingly, the invention provides methods and apparatuses suitable for delivery of one or more therapeutic modalities in a selective fashion.

For convenience, certain terms employed in the specification, examples, and appended claims are collected here.

The term "proliferative disorder" is recognized in the art, and, as used herein, refers to a disorder including or characterized by rapid or abnormal cell growth or proliferation. Exemplary proliferative disorders include, but are not limited to, tumors, e.g., cancerous tumors; restenosis, e.g., regrowth of smooth muscle cells of blood vessels after angioplasty; abnormal angiogenesis; hyperplasia, e.g., benign prostatic hyperplasia; and the like.

The term "treatment fluid," as used herein, refers to a fluid used for therapy of a proliferative disorder. Treatment fluids include chemotherapy fluids such as are conventional in the art, as well as fluids suitable for radiation therapy (brachytherapy), e.g., fluids comprising a radioisotope useful in treatment of proliferative disorders.

The term "treatment fluid receptacle," as used herein, refers to a receptacle or chamber adapted for receiving a treatment fluid. Treatment fluid receptacles are known in the art, and include injection ports and similar devices. A "small-volume" treatment fluid receptacle has a volume or hold-up less than conventional treatment fluid receptacles, e.g., less than about 5 ml, more preferably less than about 2 ml, and still more preferably less than 1.5 ml. Thus, treatment fluid receptacles having little dead space or low hold-up volumes are generally preferred for use in the methods and devices of the invention. Particularly preferred treatment fluid receptacles can be flushed with a small volume of flush fluid, as described in more detail below.

The term "diffusion barrier," as used herein, refers to an element adapted for decreasing or preventing diffusion or flow of fluid from a balloon into the catheter lumen or treatment fluid receptacle of the subject inflatable treatment device.

A balloon that maintains a "substantially constant shape," as used herein, refers to a balloon that maintains substantially a single shape or profile over a range of inflation sizes. Thus, for example, a balloon that maintains a substantially spherical shape upon inflation has a generally spherical shape over a range of inflation sizes, from low inflation to full inflation, and does not generally change shape as inflation is increased or decreased. It will be understood by the skilled artisan, however, that the initial shape of a balloon can be chosen to minimize the size or profile of the deflated balloon, e.g., to ease insertion of the balloon into a body cavity. Thus, a balloon can have an initial shape different from a "substantially constant shape," and still assume a "constant shape" after partial inflation. A "predetermined shape" refers to a shape that can be selected by the practitioner before balloon insertion, e.g., a shape chosen to ensure compliance of the balloon body to a selected surface, e.g., a cavity surface.

The term "narrow flow segment", as used herein, refers to a narrowed or restricted portion of a flow path. Preferably, a narrow flow segment has a flow passage sufficiently small to slow or prevent significant flow or diffusion of a fluid through the passage without application of pressure.

The term "malleable element," as used herein, refers to an element, e.g., a wire, that is malleable or flexible, i.e., capable of being shaped by bending, flexing, pressing and the like, and maintaining, temporarily or permanently, the shape thus provided. In preferred embodiments, a malleable element can be shaped by hand, e.g., by a surgeon performing a surgical procedure, to impart a selected shape to the malleable element and to the catheter of which it forms a part.

The term "flushing fluid," as used herein, refers to fluid that can be used to flush, rinse, or wash a flow portion of an inflatable treatment device. A flushing fluid can be inert, e.g., a saline solution, or can itself be a treatment fluid. In general, an inert flushing fluid is preferred.

The term "patient," as used herein, refers to an animal in need of treatment for, or susceptible to, a proliferative disorder. In preferred embodiments, the patient is a warm-blooded animal, more preferably a mammal, including humans and non-human mammals such as dogs, cats, pigs, cows, sheep, goats, rats, and mice. In a particularly preferred embodiment, the subject is a human.

The inflatable treatment devices of the invention provide certain advantages over devices known in the art. The subject devices are adaptable to a wide variety of therapeutic treatments, and are simple and safe to use. In general, the devices are implanted in a patient's body such that the balloon is in close proximity to the site to be treated, e.g., the tumor, blood vessel, and the like. In one embodiment, the balloon is placed in a natural body cavity or a cavity resulting from surgical removal or displacement of tissue, e.g., surgical debulking of at least a portion of a tumor, or angioplasty to displace or compress a growth of a blood vessel.

Thus, for example, FIG. 1 shows a cross-sectional view of an inflatable device of the invention when implanted in a body cavity. In this embodiment, the device 10 is implanted below the skin 12 in a cavity 13 formed in the patient's tissue 14. The device 10 includes an injection port 20 which has an elastomeric seal 22 secured thereto. A balloon 24 is disposed in the cavity 13 and fluidly connected to the injection port 20 through a catheter 26, which includes a malleable element 28. The balloon is filled with a treatment fluid 30, which fluid is prevented from flowing back from the balloon 24 into the catheter 26 by a diffusion barrier 32.

In certain embodiments, a treatment fluid receptacle is implanted subcutaneously, permitting ready injection of a treatment fluid while allowing healing of a surgical incision. Treatment fluid receptacles suitable for use in the devices of the invention are known in the art. For example, injection ports, which can be subcutaneously implanted, have been described in, e.g., U.S. Pat. Nos. 4,816,016 and 4,681,560 to Schulte, and are commercially available (e.g., from C. R. Bard Co.). An injection port for implantation in vivo should be constructed of materials that will not provoke an immune response or tissue reaction. An injection port preferably has an elastomeric seal secured to a base and defining an injection chamber of predetermined volume. The elastomeric seal can be adapted to sealingly engage a needle that pierces the seal, e.g., a hypodermic needle, and to reseal when the needle is removed, thereby preventing leakage. In general, preferred treatment fluid receptacles can be readily and efficiently flushed with a small volume of flush fluid, e.g., can be flushed with less than about 5 ml of flush fluid, more preferably less than about 2 ml, and still more preferably less than 1.5 ml. The amount of flush fluid required will be determined, at least in part, by such factors as the total volume of the treatment fluid receptacle, the amount of "dead space" in the treatment fluid receptacle, the nature of the treatment fluid and the flush fluid, and the like. In preferred embodiments, the volume of the treatment fluid receptacle, e.g., the injection chamber, is minimized, e.g., has a small volume. By providing a small-volume treatment fluid receptacle, the volume of treatment and flushing fluids is minimized, preventing overinflation of the balloon and decreasing the volume of fluids that must be handled by the physician. Preferred treatment fluid receptacles have a volume of at least 0.5 ml, but not more than 5 ml, more preferably between about 1 and about 3 ml. In general, it is desirable for the injection port to be palpable through the skin, so that it can be easily located. The treatment fluid receptacle can be at least partially opaque to X-rays, permitting localization by radiography.

As mentioned above, in certain embodiments it is desirable, after treatment fluid has been injected into the treatment device, to flush the injection port to displace a treatment fluid from the injection port and catheter. For example, when the treatment fluid is a radioactive fluid, it is desirable to prevent radiation damage to healthy tissue adjacent to the treatment fluid receptacle and along the catheter path. To prevent damage to healthy tissue, the treatment fluid can be flushed out of the injection port and away from such tissue. The flush fluid can be flushed through the catheter and into the balloon, thereby flushing the catheter and increasing the amount of radioactive material in the balloon. A small-volume treatment fluid receptacle can be flushed rapidly and completely using small volumes of flush solution, thereby reducing the amount of additional fluid added to the balloon. Thus, a small-volume treatment fluid receptacle is preferred for use with radioactive treatment fluids. Alternatively, the flush fluid can be removed from the treatment device, e.g., by use of a needle, positioned in the injection port, for withdrawing excess fluid. In this embodiment, two needles can be employed simultaneously: one needle for injection of a flush fluid into the injection port, and a second needle for removal of the fluid. In this embodiment, further inflation of the balloon can be prevented.

The inventive devices can include a diffusion barrier, to prevent unwanted backflow of treatment fluid from the balloon into the catheter. The diffusion barrier thereby prevents premature deflation of the balloon and isolates the treatment fluid in the balloon. In particular, the diffusion barrier can reduce or prevent diffusion or flow of a treatment fluid, especially a radioactive treatment fluid, from the balloon into the catheter or other parts of the implantable device, thereby preventing damage to healthy tissue adjacent to the catheter track. The diffusion barrier can be any element or elements adapted to retard or prevent fluid flow, including, without limitation, a valve (e.g., a check valve) or other flow regulating element, a narrow flow segment, and the like. A valve can be manually or automatically operated to permit control of fluid flow, if desired, e.g., during balloon filling, flushing of an injection port, or removal of fluid from the device. In certain embodiments, the diffusion barrier is an elastomeric material disposed in the fluid flow path and having a slit, e.g., a slit of proportions similar to a Holter valve opening. In this embodiment, fluid flow through the diffusion barrier can be accomplished by the application of fluid under pressure, e.g., by providing a fluid under pressure with a hypodermic syringe, causing the elastomer to yield sufficiently to permit fluid flow. Preferably, the pressure required to cause fluid flow through the diffusion barrier is not so high as to present risk of rupture of the therapeutic device, but is sufficient to reduce unwanted flow from the balloon. The diffusion barrier can provide resistance to fluid flow in one direction (e.g., a one-way check valve) or in both directions. However, the diffusion barrier is preferably adapted to allow removal of fluid from the balloon when the therapeutic procedure is complete, preferably without requiring removal of the balloon from the body cavity. Thus, in certain embodiments, the diffusion barrier is not a check valve. The diffusion barrier can reduce or eliminate flow from the balloon for at least a short period of time, e.g., sufficient time for therapeutic treatment to be completed.

In certain embodiments, the inventive apparatus can include a malleable element extending through at least a portion of the length of the catheter lumen. Thus, the malleable element is preferably adapted to confer a shape upon at least a portion of the catheter length. The malleable element is preferably an integral component of the catheter, and is not a stylet or guidewire. The malleable element can provide increased stiffness to the catheter, thereby preventing kinking of the catheter and concomitant blockage of the lumen, during insertion or removal. In particular, the malleable element can eliminate the need for a separate guidewire or stylet for inserting the catheter, simplifying surgical procedures. However, the malleable element should not be excessively rigid, to avoid damaging fragile tissues. The malleable element further can permit a shape to be temporarily or permanently imparted to the catheter. Thus, the catheter can be easily and accurately placed in the patient's body. For example, the malleable element can be conformed to a shape of a body lumen, or can be formed to permit the balloon to be placed at a body site not readily accessible by conventional means. Also, the malleable element can provide a means for securing or anchoring the implantable device in a patient's body and preventing the catheter from "backing out" during or after surgical placement.

Figure 2A:
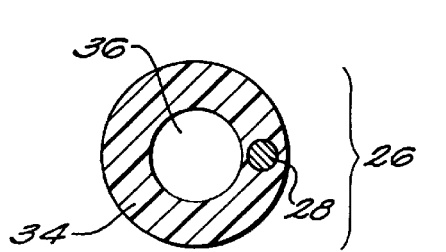
FIGS. 2A and 2B show cross-sectional views along the line 2—2' of embodiments of the catheter of the invention.
Figure 2B:
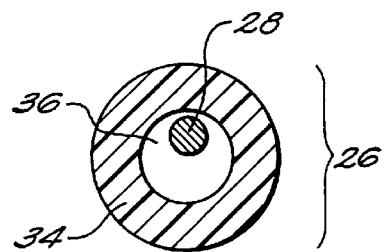

The malleable element can comprise, a flexible wire, which can be embedded in a wall of the catheter, secured to an inner or outer surface of a sidewall of the catheter, or can be situated in the lumen of the catheter. Thus, for example, FIG. 2A depicts a cross-sectional view of one embodiment of a catheter along line 2—2 of FIG. 1. The sidewall 34 of the catheter 26 defines a catheter lumen 36. A malleable wire 28 is embedded in the sidewall 34. FIG. 2B depicts a catheter in which a malleable element 28 is secured to the sidewall 34 in the catheter lumen 36 of catheter 26. The wire can be made of, stainless steel, titanium and other metals, and alloys thereof. A preferred malleable element is a titanium wire, e.g., a 20 mil annealed titanium wire. In one embodiment, the malleable element comprises a metallic element or alloy, such as nitinol, which exhibits "shape memory," i.e., has the property of returning to a predefined shape upon heating. In this embodiment, the wire can be selected to have a desired shape when implanted, but can be bent to a different shape prior to insertion to accommodate placement in vivo, and then heated (e.g., with a resistive heater) to restore the preselected shape. In certain preferred embodiments, the malleable element comprises a metallic element or alloy which does not substantially interfere with NMR measurements, e.g., magnetic resonance imaging; i.e., NMR measurements of the patient's body can be performed while the malleable element is present in the patient's body. In this embodiment, non-ferromagnetic metals or alloys are preferred. A preferred malleable element comprises an annealed titanium wire, preferably about 20 mil in diameter.

Such a wire can also be employed to provide a source of electric current, e.g., to a resistive heater, or to provide means for monitoring conditions, e.g., temperature, inside the patient's body. Thus, a malleable wire can provide means for additional treatment modalities, e.g., heat therapy, which can be employed in conjunction with chemotherapy and brachytherapy, if desired. Additionally, the malleable element can be employed as a radio-opaque marker for locating the catheter in the body.

The inflatable treatment devices include an inflatable balloon for containing a treatment fluid in close proximity to the tissue to be treated. It will be understood that the term "balloon" is intended to include distensible devices which can be, but need not be, constructed of an elastic material. A variety of balloons or other distensible devices for use with surgical catheters are known in the art and are contemplated for use in the invention; many balloons are commercially available. In one embodiment, the balloon is constructed of a material that is substantially impermeable to the active components of the treatment fluid with which it is filled, and is also impermeable to body fluids, e.g., blood, cerebrospinal fluid, and the like. An impermeable balloon is useful in conjunction with a radioactive treatment fluid, to prevent the radioactive material from escaping the treatment device and contaminating the surgical field or tissues of the patient. In another embodiment, the balloon is permeable to the treatment fluid, and permits the fluid to pass out of the treatment device and into a body lumen or cavity. A permeable balloon is useful when the treatment fluid is a chemotherapeutic agent which must contact tissue to be effective. Semi-permeable balloons can also find use in the inventive devices. For example, a semipermeable material that is capable of preventing the passage of a radioactive material through the balloon wall can be used to contain a radioactive treatment fluid, where certain fluid components can pass through the membrane while the radioactive component is retained within the balloon. In some embodiments, isotonic fluids are preferred for use in semipermeable balloons, as discussed below. Silicone, e.g., NuSil, is a preferred material for a balloon wall.

In general, it is preferable that the balloon have a shape that permits the balloon to conform to the body cavity or lumen in which the balloon is to be inflated. For example, a generally spherical cavity can be filled with a substantially spherical balloon, while an elongated balloon shape is suitable for an elongated body lumen such as a blood vessel. Irregular balloon shapes may also find application in the subject devices and methods. In certain embodiments, a balloon will be selected such that, upon inflation, the balloon does not compress the tissue which is being treated, or surrounding tissues. Thus, when a radioactive treatment fluid is introduced into the device, e.g., by injection, the inflatable treatment device is inflated to a volume not substantially greater than a volume of the body cavity in which the device has been placed, thereby avoiding any substantial compression or distortion of normal tissue. For example, in one embodiment, when the balloon is placed within a cavity left by surgical removal of tissue, the balloon is not inflated to a size substantially larger than the size of the cavity. However, in certain embodiments, the balloon preferably is inflated to compress tissue. For example, when the proliferative disorder being treated is, e.g., restenosis of a blood vessel, the balloon can be inflated to a size large enough to compress the excess tissue, while also providing chemotherapy, brachytherapy, or the like to treat the lesion. Thus, a balloon can be selected to have a desired size, and the amount of treatment fluid can be adjusted to attain an inflation of the balloon to achieve the desired size. In general, the balloon should have a small profile, e.g., a small size, when deflated, to permit facile placement in the patient's body and to minimize the size of a surgical incision needed to place the balloon at the desired site of action.

In some embodiments, a balloon is attached to the catheter at substantially a single point on, or a single side of, the balloon body. Catheters suitable for use in the invention are well known in the art. A preferred catheter material is radio-opaque silicone. Attachment of a balloon to a catheter at a single point on the balloon body permits the balloon (e.g., a spherical balloon) to maintain a substantially constant (e.g., spherical) shape over a range of inflation volumes. That is, the balloon is not constrained in shape by multiple attachment points to the catheter, as is commonly the case with, e.g., balloons for Foley catheters. In other embodiments, the balloon is attached to the catheter at multiple points on the balloon body, while allowing the balloon to maintain a constant shape over a range of inflation sizes. For example, a balloon attached to a catheter at both distal and proximal points on the balloon body can be unconstrained upon inflation where the catheter includes an expansion element (e.g., a slidable engagement element) that permits the catheter to adjust in length as the balloon expands or contracts. A balloon which maintains a substantially constant shape over a range of inflation volumes permits a surgeon to select a balloon to conform to a cavity of a particular shape with less concern over the size of the cavity. Thus, devices that include such a balloon reduce the need for the surgeon to prepare several different-sized balloons prior to surgery.

The invention also contemplates the use of multiple balloons, e.g., a double-walled balloon. Such a balloon can comprise, for example, an impermeable inner wall and a permeable outer wall. In this embodiment, the inner balloon can be filled with, e.g., a radioactive treatment fluid, while the outer balloon (i.e., the space between the inner and outer balloon walls) is filled with a chemotherapeutic treatment fluid. This embodiment allows two modes of therapy (e.g., chemotherapy and brachytherapy) to be administered simultaneously with a single device. In this double-walled balloon embodiment, the device preferably includes two treatment fluid receptacles, one in communication with each of the two balloons, preferably through a separate catheter, one catheter fluidly connected to each balloon and treatment fluid receptacle. The two balloons can thus be inflated with two treatment fluids at the same time or at different times during therapy. Inflation of an inner balloon can provide pressure on an outer balloon, which can cause the outer balloon to expand, or can force or urge fluid in the space between the inner and outer balloon walls through the membrane of a porous outer balloon. Higher-order balloons, e.g., triple-walled balloons, can also be used in the inventive devices.

Figure 3:
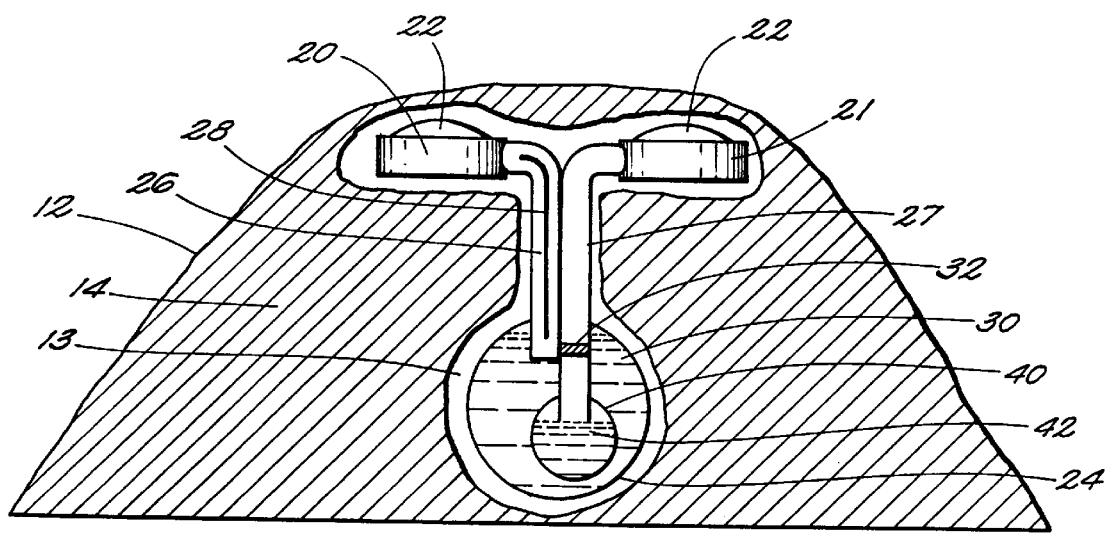
FIG. 3 is a schematic cross-sectional view of a double-balloon embodiment of a treatment device of the invention.

Thus, for example, FIG. 3 shows a double-balloon device of the invention. The device has two treatment fluid receptacles 20, 21, each having an elastomeric seal 22 secured thereto. Receptacle 20 is fluidly connected to outer balloon 24 through catheter 26, which includes a malleable element 28, and receptacle 21 is fluidly connected to inner balloon 40 by catheter 27, which includes diffusion barrier 32. The device of FIG. 3 is useful where a chemotherapeutic fluid 30 is used to inflate the outer balloon 24, while a radioactive fluid 42 fills the inner balloon 40. Diffusion barrier 32 prevents flow of the radioactive fluid 42 from the balloon 40 to the catheter 27.

The catheter element can be any of a variety of catheters known in the art. A preferred catheter material is silicone, preferably a silicone that is at least partially radio-opaque, thus facilitating x-ray location of the catheter after implantation of the device. The catheter can also include conventional adapters for attachment to the treatment fluid receptacle and the balloon, as well as devices, e.g., right-angle devices, for conforming the catheter to contours of the patient's body.

In some embodiments, the inventive devices are provided in pre-assembled form, i.e., the components are assembled in advance of a surgical insertion procedure. In certain embodiments, however, the inventive devices are configured to permit modular assembly of components, e.g., by a surgeon. Thus, for example, a treatment fluid receptacle can be provided with an element adapted for connection to any one of a plurality of catheters. The connection element can be, e.g., any element known in the art for effecting connection between components such as catheters, injection ports, and the like. Illustrative connectors include luer adapters and the like. In this embodiment, a variety of catheters and balloons can be provided, each of which is adapted for facile connection to the treatment fluid receptacle. The surgeon can then select an appropriate size and shape of balloon for treatment of a particular proliferative disorder without need for providing several treatment fluid receptacles. The catheter and balloon can be selected according to the results of pre-operative tests (e.g., x-ray, MRI, and the like), or the selection can be made based on observation, during a surgical procedure, of the target cavity (e.g., a surgical cavity resulting from tumor excision). When the surgeon selects an appropriate balloon (e.g., a balloon having a size and shape suitable for placement in a body cavity), the catheter and balloon can then be attached to the pre-selected treatment fluid receptacle, thereby assembling the treatment device.

The above-described implantable inflatable treatment devices can be employed in the treatment of proliferative disorders in a patient. In one aspect, the invention provides a method of treating proliferative disorders including the step of implanting in the patient's body an inflatable treatment apparatus, in which the apparatus includes a small-volume treatment fluid receptacle for receiving a treatment fluid; an inflatable balloon having a balloon body; a catheter connected between the treatment fluid receptacle and the balloon and defining a fluid flow path therebetween; and a diffusion barrier disposed in the fluid flow path between the treatment fluid receptacle and the balloon; wherein the balloon is secured to the catheter such that the balloon maintains a substantially constant shape during inflation; and introducing a treatment fluid into the treatment fluid receptacle so that the balloon is inflated, such that the proliferative disorder is treated. In certain embodiments, the method includes the step of selecting a balloon for treatment a proliferative disorder in a patient. In some embodiments, the method includes, prior to the implanting step, the further step of assembling an inflatable treatment apparatus.

The treatment devices of the invention (or any part thereof, e.g., the balloon) can be implanted according to surgical methods well known to the skilled artisan. In one embodiment, the balloon is implanted in a cavity formed by removal of tissue from a tumor or organ. Thus, in certain embodiments, the method includes the step of surgically removing tissue to form a cavity in the patient's body prior to implanting the inflatable device. In other embodiments, the device is implanted in a natural body cavity, e.g., in the abdominal cavity, or an organ such as a lung, uterus, or prostate gland. In yet other embodiments, a cavity or space, for placement of the inventive device in a patient's body, can be formed by displacing, compressing, or otherwise repositioning tissue, without surgically removing tissue. Illustratively, tissue can be compressed, e.g., by inflation of a balloon, prior to placement of a device of the invention in the cavity formed thereby. In certain embodiments, the treatment fluid receptacle is implanted subcutaneously. It will be appreciated that the catheter or catheters of the device can be implanted so as to pass through a body wall, e.g., the skull, the abdominal wall, and the like.

The treatment fluid (or fluids) for inflating the balloon (or balloons) can be provided to the treatment fluid receptacle by, e.g., transcutaneous injection into an injection port(s). Injection can be with a syringe, e.g., a hypodermic syringe, or with a pump or other mechanical delivery means.

In certain preferred embodiments, the proliferative disorder is a tumor, more preferably a solid tumor, including both benign and malignant tumors. In some embodiments, the tumor is a cancerous tumor. Methods of the invention are useful in treating cancers such as, without limitation, brain tumors, breast tumors, prostate tumors, ovarian tumors, and the like. In another preferred embodiment, the proliferative disorder is restenosis, e.g., of a blood vessel. Thus, the subject method can be employed to treat or to prevent restenosis in a patient. Similarly, the subject method can be employed to treat hyperplasia, including endometriosis, benign prostatic hyperplasia, and the like.

In certain embodiments, the treatment fluid includes a chemotherapy agent. Formulation and dosage of chemotherapy agents is routine to the skilled artisan. In certain embodiments, the treatment fluid includes a radioisotope. Radioactive treatment fluids are useful for brachytherapy, as discussed supra. Preferred radioisotopes for brachytherapy include $^{90}Y$, $^{198}Au$, $^{32}P$, $^{125}I$, and $^{131}I$. Radioisotope preparations suitable for use in the subject treatment devices are known to those of skill in the art. It will be appreciated that a treatment fluid can be formulated to provide more than one treatment modality. For example, a chemotherapy fluid can be heated to provide both chemotherapy and heat therapy. In certain embodiments, the treatment fluid is approximately isotonic with body fluids; that is, the tonicity (ionic strength) of the treatment fluid is close to that of physiological fluids. Use of isotonic treatment fluids avoids transfer of solutions across the balloon body membrane, thereby preventing unexpected or undesired inflation or deflation of the balloon, or dilution or concentration of the treatment fluid.

In certain embodiments, the method of treatment includes the further step of flushing the treatment fluid receptacle (e.g., the injection port) with a flush fluid. As previously described, it is important to avoid damaging healthy tissue by exposure to high doses of radiation from the treatment fluid. Thus, to prevent damage to tissue adjacent the injection port and the catheter, the injection port and catheter can be flushed with a non-radioactive flush fluid. In certain embodiments, the flush fluid is flushed into the balloon. In this embodiment, the volume of flush fluid should be carefully regulated to ensure that the balloon does not become overinflated. In certain embodiments, the flush fluid inflates the balloon by no more than 20%, more preferably no more than 10%. Alternatively, the flush fluid can be withdrawn from the treatment device, e.g., by removal with a needle introduced into the injection port. In this embodiment, the balloon is preferably not significantly further inflated, e.g., inflation due to the flush solution is less than 10%, more preferably less than 5%, of the volume of the inflated balloon. In some preferred embodiments, e.g., where a radioactive treatment fluid has been employed, the flushing step can reduce the level of radioactivity present in the treatment fluid receptacle or the catheter by at least about 50%, more preferably by at least 80%, and still more preferably by at least 90%.

In certain embodiments, the flush solution has approximately physiological tonicity. In some embodiments, the flush solution is more viscous than the treatment fluid such that the flow of the flush fluid approaches plug flow. A viscous flush solution can also prevent backflow or diffusion of a radioactive treatment fluid because the higher viscosity impedes flow in the catheter lumen.

The treatment is preferably continued until the proliferative disorder has been significantly ameliorated, e.g., if the proliferative disorder is a tumor, treatment is continued until the tumor has decreased in size by at least about 10%, more preferably at least about 20%. The inflatable device can be left in place and repeated filled with treatment fluid, if desired. For example, repeated doses of a chemotherapy fluid can be administered without disturbing the placement of the device, simply by injecting more treatment fluid into a permeable balloon after-the original dose has passed through he balloon. Similarly, a radioactive fluid can be removed, e.g., to prevent excessive doses of radiation or when the radioisotope has decayed, and replenished by addition of fresh radioisotope solution. Where it is desired to use repeated doses, the strength of the doses can be varied, for example, a first, strong dose, followed by a second, less potent dose. Determination of appropriate dosages strengths and treatment regimens will be routine for the skilled artisan.

The contents of each patent, patent application, and publication cited herein are hereby incorporated by reference.

Those skilled in the art will recognize, or be able to ascertain using no more than routine experimentation, numerous equivalents to the methods and devices described herein. Such equivalents are considered to be within the scope of this invention and are covered by the following claims.

What is claimed is:

1. An implantable apparatus for treating a proliferative disorder in a patient, comprising:
   a treatment fluid receptacle for receiving a treatment fluid;
   an inflatable balloon having a balloon body;
   a catheter connected between the treatment fluid receptacle and the balloon and defining a fluid flow path therebetween; and
   a diffusion barrier disposed in the fluid flow path between the treatment fluid receptacle and the balloon.

2. The apparatus of claim 1, wherein the treatment fluid receptacle has a small volume and is adapted to be implanted subcutaneously in the body of the patient.

3. The apparatus of claim 1, wherein the diffusion barrier is a narrow flow segment.

4. The apparatus of claim 1, wherein the balloon has a substantially spherical shape when inflated.

5. The apparatus of claim 1, wherein the balloon is secured to the catheter at substantially a single point on the balloon body.

6. The apparatus of claim 1, wherein the balloon is secured to the catheter at a plurality of points on the balloon body.

7. The apparatus of claim 1, wherein the catheter further comprises a malleable element.

8. The apparatus of claim 1, wherein the balloon body is substantially impermeable to the treatment fluid.

9. The apparatus of claim 1, wherein the balloon comprises a semipermeable membrane.

10. The apparatus of claim 1, wherein the treatment fluid receptacle is sized and dimensioned for being flushed with a flushing fluid without substantially expanding the balloon.

11. The apparatus of claim 1, wherein the balloon is secured to the catheter such that the balloon maintains a pre-selected shape during inflation.

12. The apparatus of claim 1, wherein the balloon comprises a double-walled balloon having an inner wall and an outer wall.

13. The apparatus of claim 1, wherein the balloon is sized and dimensioned for placement in a blood vessel.

14. The apparatus of claim 1, wherein the balloon is sized and dimensioned for placement in a cavity left by surgical removal of a tumor from the patient.

15. The apparatus of claim 1, wherein the balloon is sized and dimensioned for placement in a natural body cavity.

16. The apparatus of claim 1, wherein the balloon is filled with a treatment fluid.

17. The apparatus of claim 16, wherein the treatment fluid is a radioactive fluid.

18. The apparatus of claim 16, wherein the treatment fluid has substantially physiological tonicity.

19. The apparatus of claim 12, further comprising a second treatment fluid receptacle.

20. The apparatus of claim 19, wherein the second treatment fluid receptacle fluidly communicates with a volume between inner and outer balloon walls.

21. An implantable apparatus for treating a proliferative disorder in a patient, comprising:
   a treatment fluid receptacle for receiving a treatment fluid;
   an inflatable balloon having a balloon body; and
   a catheter connected between the treatment fluid receptacle and the balloon and defining a fluid flow path therebetween;
   wherein the catheter further comprises a malleable element.

22. The apparatus of claim 21, wherein the malleable element does not substantially interfere with NMR analysis.

23. The apparatus of claim 21, wherein the balloon is sized and dimensioned for placement in a blood vessel.

24. An implantable apparatus for treating a proliferative disorder in a patient, comprising:
   a treatment fluid receptacle for receiving a treatment fluid;
   an inflatable balloon having a balloon body;
   a catheter connected between the treatment fluid receptacle and the balloon and defining a fluid flow path therebetween; and
   a diffusion barrier disposed in the fluid flow path between the treatment fluid receptacle and the balloon;
   wherein the treatment fluid receptacle is adapted to be flushed with a small volume of a flush fluid.

25. A method for treating a proliferative disorder in a patient, the method comprising the steps of:
   implanting in the patient's body an inflatable treatment apparatus, the apparatus comprising:
      a treatment fluid receptacle for receiving a treatment fluid;
      an inflatable balloon having a balloon body;
      a catheter connected between the treatment fluid receptacle and the balloon and defining a fluid flow path therebetween; and
      a diffusion barrier disposed in the fluid flow path between the treatment fluid receptacle and the balloon; and
   introducing a treatment fluid into the treatment fluid receptacle such that the balloon is inflated;

such that the proliferative disorder is treated.

26. The method of claim 25, further comprising the step of flushing the treatment fluid into the balloon.

27. The method of claim 25, wherein the treatment fluid is flushed into the balloon with a flush fluid.

28. The method of claim 27 wherein the flush fluid further inflates the balloon by no more than 10% of the balloon volume prior to the flushing step.

29. The method of claim 25, wherein the implanting step comprises the step of positioning the inflatable balloon adjacent to a tumor.

30. The method of claim 29, wherein the implanting step comprises the step of positioning the inflatable balloon adjacent to a solid tumor.

31. The method of claim 29, wherein the implanting step comprises the step of positioning the inflatable balloon adjacent to a cancerous tumor.

32. The method of claim 29, wherein the implanting step comprises the step of positioning the inflatable balloon adjacent to a brain tumor.

33. The method of claim 29, wherein the implanting step comprises the step of positioning the inflatable balloon adjacent to a breast tumor.

34. The method of claim 25, further comprising, prior to the implanting step, the step of surgically creating a cavity in the patient's body.

35. The method of claim 25, further comprising, prior to the implanting step, the step of selecting a balloon for treating the proliferative disorder.

36. The method of claim 35, further comprising, prior to the implanting step, the step of assembling the inflatable treatment apparatus.

37. The method of claim 25, wherein the apparatus is implanted in a natural body cavity.

38. A method for treating a proliferative disorder in a patient, the method comprising:

determining a characteristic of a cavity in the patient's body, the characteristic being selected from the group consisting of volume, shape, or a dimension;

selecting an inflatable balloon suitable for placement in the cavity, the balloon including a balloon body;

implanting in the cavity an inflatable treatment apparatus comprising:

a treatment fluid receptacle for receiving a treatment fluid;

the inflatable balloon;

a catheter connected between the treatment fluid receptacle and the balloon and defining a fluid flow path therebetween;

a diffusion barrier disposed in the fluid flow path between the treatment fluid receptacle and the balloon; and introducing a treatment fluid into the treatment fluid receptacle such that the balloon is inflated;

such that the proliferative disorder is treated.

39. The method of claim 38, wherein the treatment fluid is a radioactive fluid.

40. The method of claim 38, wherein the treatment fluid is a chemotherapy fluid.

41. The method of claim 38, the method comprising, prior to the implanting step, the further step of assembling the inflatable treatment apparatus.

42. An implantable apparatus for treating a proliferative disorder in a patient, said apparatus comprising:

a treatment fluid receptacle for receiving a treatment fluid;

an inflatable balloon having a balloon body;

a catheter connected between said treatment fluid receptacle and said balloon, said catheter defining a fluid flow path therebetween; and a narrow flow segment disposed in said fluid flow path between said treatment fluid receptacle and said balloon.

43. An implantable apparatus for treating a proliferative disorder in a patient, said apparatus comprising:

a treatment fluid receptacle for receiving a treatment fluid;

an inflatable balloon having a balloon body;

a catheter connected between said treatment fluid receptacle and said balloon, said catheter defining a fluid flow path therebetween;

a malleable element coupled to said catheter, and a diffusion barrier disposed in the fluid flow path between said treatment fluid receptacle and said balloon.

* * * * *